United States Patent [19]

Cowan

[11] 4,297,506

[45] Oct. 27, 1981

[54] SYNTHESIS OF ESTERS

[75] Inventor: Kiplin D. Cowan, Bartlesville, Okla.

[73] Assignee: Phillips Petroleum Co., Bartlesville, Okla.

[21] Appl. No.: 110,302

[22] Filed: Jan. 8, 1980

[51] Int. Cl.$^3$ .................. C07C 67/04; C07C 31/20
[52] U.S. Cl. ................................. 560/246; 568/858
[58] Field of Search ............... 568/858; 560/244, 236, 560/237, 246

[56] References Cited

U.S. PATENT DOCUMENTS

| | | | |
|---|---|---|---|
| 2,739,173 | 3/1956 | Corey et al. | 568/858 |
| 3,510,500 | 5/1970 | Walsh | 560/237 |
| 3,720,704 | 3/1973 | Sakomura | 560/237 |
| 3,968,177 | 7/1976 | Kaufhold | 560/236 |
| 4,000,185 | 12/1976 | Kurkov et al. | 560/237 |
| 4,001,307 | 1/1977 | Cardenas | 560/237 |
| 4,026,924 | 5/1977 | Stapp | 560/246 |
| 4,044,041 | 8/1977 | Stapp | 560/246 |
| 4,113,971 | 9/1978 | Stapp | 560/246 |
| 4,164,616 | 8/1979 | Childs | 568/858 |

*Primary Examiner*—Joseph E. Evans

[57] ABSTRACT

An organic ester is produced by conversion of an organic halide employing excess alkali metal carboxylate. A resultant reaction mass including solids comprised of alkali metal halide is obtained containing occluded in the solids portion an amount of otherwise difficult-to-recover desired ester product. At least a portion of said solids is recycled to the conversion whereby to prevent further occlusion of desired product. In an embodiment of the invention, potassium acetate salt is recycled for reuse.

4 Claims, No Drawings

SYNTHESIS OF ESTERS

BRIEF SUMMARY OF THE INVENTION

In the production of an organic ester by conversion of an organic halide employing an excess of an alkali metal carboxylate wherein the resultant reaction mass includes solids which retain occluded therein an appreciable quantity of desired ester product, the step of recycling at least a portion of said solids whereby to reduce the loss of ester product to said solids.

DETAILED DESCRIPTION

This invention relates to an improvement in the production of an alkanediol.

In U.S. Pat. No. 4,164,616, issued Aug. 14, 1979, by William V. Childs, there is described and claimed the production of an alkanediol which comprises bringing together a conjugated diene, a halogen, an alkali metal acetate and an acid under conditions to form a diacetoxyalkene, the diacetoxyalkene is hydrogenated to form diacetoxyalkane which is hydrolyzed to the corresponding alkanediol.

In one of its aspects the invention relates to an improvement in a step of the process just described. More specifically, in the process just described, the diacetoxyalkene and acid are separated by distillation from the reaction mass leaving behind a residue containing alkali metal acetate and alkali metal halide in which there is included a significant quantity or proportion of the desired diacetoxyalkene product.

In one of its concepts the present invention provides an improvement in the process described herein which comprises essentially having present in the reaction zone in which the diacetoxyalkene is formed a sufficient portion or amount of the residue occluding diacetoxyalkene to avoid occlusion of further quantities thereof. In this concept of the invention the distillation residue is simply recycled to the reaction zone.

In a further concept of the invention it relates to a four step continuous process for making alkanediols wherein during the first step of converting dihaloalkenes to diacetoxyalkenes, residues comprised of excess reactant salts, by-product salt, and occluded diacetoxyalkenes are recycled without washing or purification thus to insure in the reaction zone as soon as possible a saturation of the capacities of the salts to occlude further quantities of diacetoxyalkene.

Diacetoxyalkenes are intermediates used in making alkanediols which are in themselves useful products. One such product, 1,4-butanediol, is a raw material in producing tetrahydrofuran (a known solvent) and a relatively new engineering plastic, polybutylene terephthalate, which has a balanced combination of physical properties with excellent moldability rarely found with other synthetic resins of this type.

Several methods are known to produce 1,4-butanediol. One such method is disclosed in said U.S. Pat. No. 4,164,616, wherein 1,4-butanediol is prepared in a 4-step continuous process by: step (1) reacting butadiene and bromine to form 1,4-dibromo-2-butene which is almost instantaneously reacted with potassium acetate to form the 1,4-diacetoxy-2-butene; step (2) hydrogenating the double bond; step (3) hydrolyzing to the corresponding diol; and step (4) electrolyzing the alkali metal halide by-product salt to liberate free bromine and alkali metal hydroxide which are then returned for use in the process.

During the acetolysis in the first step, some by-product salt as well as excess alkali metal acetate is obtained as a residue from the distillation of the 1,4-diacetoxy-2-butene. This residue also contains by occlusion about 50 wt. % of the liquid product 1,4-diacetoxy-2-butene which cannot be further removed by solvent washing because of similarities in polarity between the solvent, reactant salt, and product. Rather than subject this residue to hydrohalogenation which could convert not only the excess alkali metal acetate but also some of the occluded 1,4-diacetoxy-2-butene liquid product, it has been discovered that this residue plus some alkali metal acetate salt obtained as a by-product from the subsequent hydrolysis step can simply be recycled without purification or separation back to the acetolysis step. This recycling eliminates the need for coverting the excess and by-product alkali metal acetate salt via hydrohalogenation to the alkali metal halide which in turn requires more energy and expense to electrolytically convert back to re-usable reactants.

It is an object of this invention to provide a process for the production of an alkanediol, e.g., 1,4-butanediol. It is a more specific object of this invention to provide a process for the improved production of a diacetoxyalkene, e.g., 1,4-diacetoxy-2-butene. A further object of the invention is to provide improved yields of a diacetoxylated alkane. Further still, an object of the invention is to provide improved quantities or yields of an alkanediol, e.g., 1,4-butanediol.

Other aspects, concepts, objects, and the several advantages of this invention are apparent from a study of this disclosure and the appended claims.

According to the invention, as described herein, the overall production of an alkanediol, e.g., 1,4-butanediol and, more specifically, the specific production of a diacetoxyalkene, is so operated that there will be in the reaction zone a sufficient amount of diacetoxyalkene occluded in the salts which occlude it to prevent further loss by occlusion of the diacetoxyalkene.

Further, according to the invention there are included the use of mono-olefin and halogen acid in lieu of diene and halogen to produce an organic halide which is then converted to an organic ester.

Still further, it is possible to use, say, a diene and halogen resulting in a tetrahalo compound.

In a broad view of the invention, there can be used olefins e.g., ethylene, propylene, butylenes, up to, say, 12 carbons in the olefin molecule, including cyclo-olefins, e.g., cyclohexene, cyclohexadiene, etc.

Various conjugated dienes can be used in the production of the product ultimately to be recovered.

Thus, as conjugated diene there can be used at least one of the following:
1,3-butadiene
isoprene
1,3-pentadiene
2,3-dimethyl-1,3-butadiene
2-ethyl-1,3-pentadiene
1,3-hexadiene
2-methyl-1,3-hexadiene
1,3-octadiene
2-methyl-1,3-undecadiene
2-methyl-3-isopropyl-1,3-butadiene The current invention is a process improvement over the aforementioned copending application pertaining to the recycling of an alkali metal organic carboxylate plus occluded products and by-products.

A. Halogenated Alkenes

The halogenated alkenes useful in this invention are those materials represented by the formula $R(X)_n$ wherein R can be any saturated or olefinically unsaturated hydrocarbyl radical varying from 2 to 12 carbon atoms, X can be an iodine or bromine radical; and n can be 1, 2, or 3. Representative of these type materials are, but not limited to, such materials as:

bromoethane
1-bromopropane
1-bromo-2-propene
1-bromobutane
2-bromobutane
2-methyl-2-bromobutane
1-bromo-2-butene
1-bromohexane
1-bromo-2-hexene
1-bromo-2-decene
1-bromo-2-dodecene
1-bromocyclohexane
1-bromo-2-cyclohexene
1,4-dibromobutane
1,2-dibromobutane
1,4-dibromo-2-butene
1,2-dibromo-3-butene
1,6-dibromo-2-hexene
1,4-dibromo-2-hexene
1,10-dibromo-2-decene
1,12-dibromo-2-dodecene
1,2-dibromo-2-cyclohexene
1,2,3-tribromopropane
1,1,3-tribromo-2-butene
1,4,6-tribromo-2-hexene
1,4,7-tribromo-2,5-heptadiene
1,2,3,4-tetrabromobutane and the like and mixtures thereof. The corresponding iodo compounds of the above materials are also included.

The preferred materials are the dibromobutenes since the invention relates to an improvement of a previously mentioned invention pertaining to 1,4-butanediol.

B. Metal Carboxylate

The metal carboxylate salts useful in this invention are those materials represented by the formula MR' wherein M can be any metal listed in Group IA or IIA of the Periodic Table such as lithium, sodium, potassium, rubidium, cesium, magnesium, calcium, strontium, and barium; and R' can be any organic carboxylic acid radical having from 1 to 4 carbon atoms such as formate, acetate, propionate, butyrate, and the like. The alkali metal and alkaline earth metal are to be read for brevity's sake as being equivalent in the process. The preferred types of materials employed are sodium or potassium acetate dissolved or dispersed in acetic acid or acetic acid/acetic anhydride mixtures.

Carboxylic Acid Solvents

The solvents useful in this invention can be formic acid, acetic acid, propionic acid, butyric acid and the like. A small amount of the corresponding carboxylic acid anhydride can also be used. It is preferred that the organic carboxylic acid solvent correspond to the anionic portion of the metal carboxylate salt to simplify solvent-salt processing, for example, potassium acetate in acetic acid, potassium propionate in propionic acid, etc.

Reaction Conditions

Reaction times, temperatures, pressures etc., should correspond to those disclosed in the U.S. Pat. No. 4,164,616.

The following examples serve to illustrate the operability of this invention. Examples I, II, and III describe steps 1, 2, and 3 of the overall 1,4-butanediol synthesis disclosed in the aforementioned patent 4,164,616. These are described to illustrate the two sources of recycled alkali metal acetate salt used in the invention. Also, in Example II $KOOCCH_3$ is used as a buffer during hydrogenation.

EXAMPLE I

This example describes the acetolysis operation in Step 1 of the overall 1,4-butanediol process and establishes the source of a residual material later used in recycling.

Into a 500 milliliter round-bottom flask was charged 91.6 grams (0.9333 moles, includes 25 mole % excess) of potassium acetate and 137.4 grams of a 10:1 (wt/wt) solution of acetic acid: acetic anhydride. The solution was magnetically stirred and electrically heated to 160° C. whereupon 80 grams (0.373 moles) or 1,4-dibromo-2-butene was added. The temperature dropped to 142° C. After about 20 minutes the mixture was analyzed by GLC from which it was calculated that a 98 wt. % yield of 1,4-diacetoxy-2-butene was obtained. The mixture was cooled to room temperature and filtered through a 10-20 micron size glass fritted funnel. The residue was washed with 200 milliliters of acetic acid and dried to give 79.2 grams (89 grams is theoretical) of potassium bromide by-product. The filtrate was distilled through a Kugelrohr distillation apparatus at about 110° C./10 mm(torr) to give 330 grams and leaving 56 grams residue. The distillate was analyzed by GLC and found to contain 11.2 wt. % 1,4 diacetoxy-2-butene (37 grams). A Kugelrohr distillation apparatus is described in Aldrich Chem. Co. Catalog 19, pg. 916. The residue from this distillation, 56 grams, was calculated to contain the excess potassium acetate used (0.1873 moles, 18.4 grams) plus the unaccounted potassium bromide by-product (9.8 grams). The balance of the residue was assumed to be 27.8 grams of 1,4-diacetoxy-2-butene. This total 56 grams of residue was recycled back into the process to make up a portion of potassium acetate employed during the acetolysis step (Step 1). This recycle is further described in Example IV.

EXAMPLE II

This example is a non-inventive run describing the second step of the overall 1,4-butanediol process, namely, the hydrogenation of 1,4-diacetoxybutene.

To the 330 grams of overhead distillate obtained in Example I was added 6 grams (0.061 moles) of potassium acetate. The potassium acetate was added as a buffer to prevent hydrogenolysis of 1,4-diacetoxy-2-butene to butyl acetate, which still slightly occurred (e.g. 2%). The mixture was then hydrogenated at about 30 to 35 psig hydrogen using 1 gram of 5 wt % palladium on alumina catalyst. The hydrogenation was carried out in about 4 equal size runs in a 500 milliliter hydrogenation bottle. After each run the mixture was decanted, washed with a little acetic acid and vacuum filtered through Celite. The filtrate was flashed distilled at 25°–50° C./10–15 mm (torr). There was obtained about 259 grams of overhead, which contained mostly acetic acid and 33.1 g residue which analyzed by GLC to be 74 wt % (24 grams) of 1,4-diacetoxybutane.

EXAMPLE III

This example is a non-inventive run describing the third step of the overall 1,4-butanediol process, namely, hydrolysis of 1,4-diacetoxybutane with potassium hydroxide. The residue from this step, which contains essentially potassium acetate by-product, is then recycled along with the residue obtained in Example I for use in the subsequent acetolysis portion of step 1 of the overall 1,4-butanediol process, thus, completing the first cycle in the current invention.

Into a 3-neck 500 milliliter round bottom flask equipped with a heating mantle, thermometer, reflux condenser, magnetic stirrer and dropping funnel was added 23 grams (0.41 moles) of potassium hydroxide and 50 milliliters of water and while being stirred the mixture was heated to 103° C. To this mixture was slowly added another mixture which contained the 33 grams residue from Example II and 10 grams of 1,4-butanediol. The mixture was stirred and heated at about 103°–107° C. for about 6 hours during which time an additional 3.3 grams (0.059 moles) of potassium acetate was added in small portions as a 50 wt % aqueous solution. GLC analysis indicated 100% hydrolysis of 1,4-diacetoxybutane to 1,4-butanediol. The reaction mixture was distilled at 25°–100° C./10 mm (torr) to remove water and 1,4-butanediol product. There was obtained by distillation, 21 grams (62% yield) of 1,4-butanediol product. The residue from this distillation (39 grams) was considered to be essentially potassium acetate although there may have been a small amount of occluded diol product. This residue was then recycled back to step 1 of the overall 1,4-butanediol process for use as a reagent in the subsequent acetolysis portion of step 1, thus completing the first cycle in the current invention.

EXAMPLE IV

This example is the basis of this invention and pertains to recycling potassium acetate salt from other steps in a multi-step process for re-use. Potassium acetate used for the acetolysis portion of step 1 of the overall butanediol process is available from three sources: (1) as an excess from the acetolysis portion of step 1 present as a distillation residue; (2) as a by-product from the hydrolysis operation of step 3; and (3) as a make-up available from the electrolytic portion of step 4. This example illustrates the use of recycle potassium acetate as it passes through steps 1, 2, and 3 of the overall butanediol. This is, thus, the first recycle of potassium acetate.

Step 1—Acetolysis:

The procedure described in Example I was repeated except 160 grams of acetic acid and 129 grams of a mixture of potassium acetate and other process materials were employed. This 129 grams was comprised of:

| Wt. | Source | Composition |
|---|---|---|
| 56g | Example I. Distillation residue | 18.4g excess KOOCCH$_3$ |
|  |  | 9.8g by-product KBr |
|  |  | 27.8g occluded 1,4-diacetoxy-2-butene |
| 39g | Example III. Distillation residue | 39.0g by-product KOOCCH$_3$ |
| 34g | Make-up | 34.0g make-up KOOCCH$_3$ |
| 129g |  | 129.0g |

The amount of KOOCCH$_3$ present was calculated to be 91.4 grams (0.9313 moles) which is a 24.8 mole % excess above the stoichiometric requirement of 0.746 moles. From the acetolysis there was obtained by GLC a 98% yield of 1,4-diacetoxy-2-butene. In addition, there was obtained in a manner previously described 83 grams (98% of theory) KBr, 415 grams of distillation overhead containing by GLC 12.7 wt % (52.7 grams) of the 1,4-diacetoxy-2-butene and 34 grams of residue. The residue from this distillation, 34 grams, was calculated to contain the excess potassium acetate used (0.1853 moles, 18.4 grams) plus the unaccounted KBr by-product (5.8 grams) plus 9.8 grams of occluded 1,4-diacetoxy-2-butene product.

Step 2—Hydrogenation:

The procedure described in Example II was repeated using the 415 grams of distillate from Example IV—step 1 plus 2 grams of KOOCCH$_3$ buffer plus 1 gram of hydrogenation catalyst. Analysis by GLC after hydrogenation was complete indicated a 97 wt % yield of 1,4-diacetoxybutane and 3 wt % yield of butyl acetate. The reaction mixture after distillation gave 256 grams distillate and 62 grams of residue containing 96 wt % (59 grams) 1,4-diacetoxybutane.

Step 3—Hydrolysis:

The procedure described in Example III was repeated using the 62 grams of bottoms from Example IV—step 2 plus 51 grams of KOH dissolved in 51 grams of H$_2$O. After hydrolysis there was obtained by distillation 26 grams of 1,4-butanediol and 73.4 grams of residue which is assumed to be essentially KOOCCH$_3$.

EXAMPLE V

This is an inventive run illustrating the use of recycled KOOCCH$_3$ in a second recycle.

Step 1—Acetolysis:

The procedure described in Example I was again repeated except 150 grams of acetic acid and 107 grams of KOOCCH$_3$ mixture was employed. This 107 grams was comprised of:

| Wt. | Source | Composition |
|---|---|---|
| 34g | Example IV - Step 1 - Dist. Residue | 18.4g excess KOOCCH$_3$ |
|  |  | 5.8g by-product KBr |
|  |  | 9.8g occluded 1,4-diacetoxy-2-butene |
| 73.4g | Example IV - Step 2 - Dist. Residue | 73.4g by-product KOOCCH$_3$ |
| 107.4g |  | 107.4g |

The amount of KOOCCH$_3$ present was calculated to be 91.8 grams (0.9313 moles) which is a 24.8% excess above the stoichiometric requirement of 0.746 moles. From the acetolysis there was obtained by GLC a 97% yield of 1,4-diacetoxy-2-butenes. In addition, there was obtained in a manner previously described 84 grams (94% of theory) KBr, 395 grams of distillation overhead containing by GLC 12.6 wt% (49.8 grams) of 1,4-diacetoxy-2-butenes and 39 grams of residue. The residue from this distillation, 39 grams, was calculated to contain the excess KOOCCH$_3$ used (0.1853 moles, 18.4 grams) plus the unaccounted KBr by-product (4.8 grams) plus 15.8 grams of occluded 1,4-diacetoxy-2-butene product.

Step 2—Hydrogenation

The procedure described in Example II was again repeated using 395 grams of distillate from the preceding step plus 2 grams of KOOCCH$_3$ buffer plus 1 gram of hydrogenation catalyst. Analysis of GLC after hydrogenation was complete indicated a 96 wt% yield of 1,4-diacetoxybutane and 4 wt% yield of butyl acetate. The reaction mixture after distillation gave 317 grams of distillate and 52 grams of residue containing 96 wt% (49.9 grams) 1,4-diacetoxybutane.

Step 3—Hydrolysis

The procedure described in Example III was again repeated but using the 52 grams of bottoms from the preceding step plus 40 grams of KOH dissolved in 60 grams of $H_2O$. After hydrolysis there was obtained by distillation 21 grams of 1,4-butanediol and 62 grams of residue which is assumed to be essentially $KOOCCH_3$.

EXAMPLE VI

This is an inventive run illustrating the use of recycled $KOOCCH_3$ in a third recycle.

Step 1—Acetolysis:

The procedure described in Example I was again repeated except 111 grams of $KOOCCH_3$ mixture was employed. This 111 grams was comprised of:

| Wt. | Source | Composition |
|---|---|---|
| 39g | Example V - Step 1 - Dist. Residue | 18.4g excess $KOOCCH_3$ <br> 4.8g by-product KBr <br> 15.8g occluded 1,4-diacetoxy-2-butene |
| 62g | Example V - Step 3 - Dist. Residue | 62g by-product $KOOCCH_3$ |

| | |
|---|---|
| 10g Make-up | 10g $KOOCCH_3$ |
| 111g | 111g |

The amount of $KOOCCH_3$ present was calculated to be 90.4 grams (0.921 moles) which is a 23.5% excess above the stoichiometric requirement of 0.746 moles. From the acetolysis there was obtained by GLC a 97% yield of 1,4-diacetoxy-2-butene. In addition, there was obtained in a manner previously described 84 grams (94% of theory) KBr, 396 grams of distillation overhead containing by GLC 14.7 wt % (58.2 grams) of 1,4-diacetoxy-2-butene and 24.3 grams of residue. The residue from this distillation, 24.3 grams, was calculated to contain the excess $KOOCCH_3$ used (0.175 moles, 17.1 grams) plus the unaccounted KBr by-product (4.8 grams) plus 2.1 grams of occluded 1,4-diacetoxy-2-butene produced.

Step 2—Hydrogenation:

The procedure described in Example II was again repeated using 396 grams of distillate from the preceding step plus 1 gram of $KOOCCH_3$ buffer plus 1 gram of hydrogenation catalyst. Analysis by GLC after hydrogenation was complete indicated a 94 wt % yield of 1,4-diacetoxybutane and 6 wt % yield of butyl acetate.

The reaction mixture after distillation gave 284 grams of distillate and 61 grams of residue containing 97 wt % (59.1 grams) of 1,4-diacetoxybutane.

Step 3—Hydrolysis:

The procedure described in Example II was again repeated but using the 61 grams from the preceding step plus 45 grams of KOH dissolved in 50 grams of $H_2O$. After hydrolysis there was obtained by distillation 27.4 grams of 1,4-butanediol and 68 grams of residue which is assumed to be essentially $KOOCCH_3$.

SUMMARY

The data disclosed herein is summarized in Tables I and II. Table I shows that residues from two steps of the multistep 1,4-butanediol process which contains potassium acetate either as excess reactant (from acetolysis step) or as by-product (from hydrolysis step) can be recycled for reuse in the acetolysis of 1,4-dibromo-2-butene in step 1 of the multistep process without reducing the yield of the product 1,4-diacetoxy-2-butene. The advantage of recycling potassium acetate is that it does not have to be washed, purified or otherwise treated before reusing. As shown by Table II, recycling potassium acetate from acetolysis has no detrimental effect on product yield. The initial run before recycling shows the lowest product yield which is believed to be due mostly to occluded liquid product particularly in the acetolysis portion of Step 1.

TABLE I

Summary. Acetolysis of
1,4-Dibromo-2-Butene Using Recycled Potassium Acetate
Charge: 80 grams 1,4-Dibromo-2-Butene
137–160 grams mixture of 10 parts by wt. acetic acid: 1 part by wt. acetic anhydride

| Example No. | Potassium Acetate, $KOOCCH_3$ | | | % Yield of 1,4-Diacetoxy-2-Butene | $KOOCCH_3$ -Cont'g Residue, Grams | |
|---|---|---|---|---|---|---|
| | $KOOCCH_3$, grams from | | % Excess | | | |
| | Fresh | Acetolysis | Hydrolysis | | | Acetolysis[a] | Hydrolysis[b] |
| I,III | 91.6 | — | — | 25 | 98 | 56 | 39 |
| IV | 34 | 56 | 39 | 24.8 | 98 | 34 | 73 |
| V | — | 34 | 73 | 24.8 | 97 | 39 | 62 |
| VI | 10 | 39 | 62 | 23.5 | 97 | 24 | 68 |

[a]Residue contains about 30–40 wt% $KOOCCH_3$
[b]Residue essentially all $KOOCCH_3$

TABLE II

Summary. Effect of Recycled Potassium Acetate on Product Yield Based on Initial 1,4-Dibromo-2-Butene Charged

| Example No. | % Yield 1,4-Butanediol |
|---|---|
| I, II, III | 62.5 |
| IV | 77.4 |
| V | 62.5 |
| VI | 80.4 |

Reasonable variation and modification are possible within the scope of the foregoing disclosure and the appended claims to the invention the essence of which is that ester occluded in the residue or salts remaining upon removal of the ester from the reaction mass, as by distillation, is recycled to the reaction in quantity sufficient to at least appreciably avoid loss of ester by occlusion, as described.

I claim:

1. In a process for producing a diacetoxyalkene from a conjugated diene, a halogen, an alkali metal acetate, and an acid wherein there is obtained in a reaction zone a reaction mass comprising alkali metal acetate, alkali metal halide, acid, and diacetoxyalkene occluded in said mass in the salts therein which cannot be separated by distillation of the non-occluded diacetoxyalkene from said mass, the steps of (1) distilling non-occluded diacetoxyalkene, and (2) recycling to the reaction zone at least a portion of said mass containing said occluded diacetoxyalkene whereby the yield of diacetoxyalkene from said reaction zone and said distillation is increased.

2. A process according to claim 1 wherein the diene is 1,4-butadiene, the halogen is one of chlorine and bromine, the alkali metal acetate is potassium acetate, the acid is acetic acid and the diacetoxyalkene is 1,4-diacetoxybutene.

3. A process according to claim 1 wherein the conjugated diene is at least one selected from 1,3-butadiene, isoprene, 1,3-pentadiene, 2,3-dimethyl-1,3-butadiene, 2-ethyl-1,3-pentadiene, 1,3-hexadiene, 2-methyl-1,3-hexadiene, 1,3-octadiene, 2-methyl-1,3-undecadiene, 2-methyl-3-isopropyl-1,3-butadiene.

4. A process according to claim 1 wherein the conjugated diene is 1,3-butadiene.

* * * * *